United States Patent [19]

Keim et al.

[11] 4,283,571

[45] Aug. 11, 1981

[54] PROCESS FOR THE CATALYTIC ISOMERIZATION OF O-CRESOL

[75] Inventors: Karl-Heinz Keim; Reinhard Kiauk, both of Wesseling; Ewald Meisenburg, Heimerzheim, all of Fed. Rep. of Germany

[73] Assignee: Union Rheinische Braunkohlen Kraftstoff Aktiengesellschaft, Wesseling, Fed. Rep. of Germany

[21] Appl. No.: 7,721

[22] Filed: Jan. 30, 1979

[30] Foreign Application Priority Data

Feb. 3, 1978 [DE] Fed. Rep. of Germany ....... 2804537

[51] Int. Cl.³ .............................................. C07C 39/07
[52] U.S. Cl. .................................... 568/783; 568/804; 252/463
[58] Field of Search ................ 260/448; 568/783, 804; 423/455, 328, 329; 252/463

[56] References Cited

U.S. PATENT DOCUMENTS

| 3,442,795 | 5/1969 | Kerr et al. | 585/269 |
| 3,655,780 | 4/1972 | Kohn et al. | 568/783 |
| 3,702,886 | 11/1972 | Argauer et al. | 260/111 |
| 3,709,979 | 1/1973 | Chu | 260/111 |
| 4,011,278 | 3/1977 | Plank et al. | 568/804 |

FOREIGN PATENT DOCUMENTS

| 874911 | 7/1949 | Fed. Rep. of Germany . | |
| 2005153 | 10/1970 | Fed. Rep. of Germany . | |
| 1956383 | 5/1971 | Fed. Rep. of Germany . | |
| 695464 | 8/1953 | United Kingdom | 568/783 |
| 748269 | 4/1956 | United Kingdom | 568/783 |
| 432123 | 11/1974 | U.S.S.R. | 568/783 |

OTHER PUBLICATIONS

Vorozhtsov et al., "J. General Chemistry", U.S.S.R. vol. 29, #7 (1959).

Primary Examiner—Werren B. Lone
Attorney, Agent, or Firm—Connolly and Hutz

[57] ABSTRACT

Isomerization of o-cresol to m-cresol by contact with a crystalline aluminosilicate zeolite of the ZSM-type, having a silica to alumina ratio greater than 5, at a temperature of about 350° to 450° C.

4 Claims, No Drawings

PROCESS FOR THE CATALYTIC ISOMERIZATION OF O-CRESOL

The invention relates to a process for the catalytic isomerisation of o-cresol using a special zeolite.

BACKGROUND OF THE INVENTION

During the catalytic methylation of phenol, the o-isomers frequently occur in a predominant proportion while the other isomers are obtained in a smaller quantity. However, a higher production of m-cresol may be desired and processes have therefore been developed for the isomerisation of the o-compounds into the corresponding m-compound. These processes are generally carried out in the presence of aluminium oxides (German Patent application No. 19 56 383) or aluminium silicates (German Patent application No. 20 05 153) as catalysts, but then disproportionation which is generally undesirable invariably occurs to a considerable extent in addition to isomerisation.

THE INVENTION

In accordance with this invention, we have now found that o-cresol can be isomerised without substantial disproportionation if the process is carried out in the presence of certain special crystalline zeolites as catalyst. The invention accordingly relates to a process for the catalytic isomerisation of o-cresol which comprises reacting o-cresol at temperatures of about 350° to 450° C. in the presence of an acidly acting crystalline aluminosilicate zeolite of the ZSM-type with a composition of oxides and water in the molar ratio of $1\pm 0.4$ M$_2$O/n-:Al$_2$O$_3$:5-100 SiO$_2$:0-60 H$_2$O, M representing a cation having a valence of n. For example, M may be an alkali metal, especially sodium, tetramethylammonium, hydrogen, metals of Group II and VIII of the Periodic Table, or mixtures of the same. An important characteristic of the crystal structure of the zeolites useful as catalysts in this invention is that they have a pore dimension greater than about 5 Angstroms and pore windows of about a size such as would be provided by 10-membered rings of oxygen atoms. The zeolites freely sorb normal hexane. In addition, their structure must provide constrained access to some larger molecules. A determination of the "constraint index" may be made by continuously passing a mixture of equal weight of normal hexane and 3-methylpentane over a small sample of zeolite at atmospheric pressure according to the following procedure. A sample of the zeolite is crushed to a particule size about that of coarse sand and mounted in a glass tube. The zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly spaced velocity over the zeolite with a helium dilution to give a helium to total hydrocarbon mole ratio of 4:1. After 20 minutes on stream, a sample of the effluent is taken and analyzed to determine the fraction remaining unchanged for each of the two hydrocarbons. The constraint index is calculated as follows:

$$\text{Constraint Index} = \frac{\log_{10} \text{(fraction of n-hexane remaining)}}{\log_{10} \text{(fraction of 3-methylpentane remaining)}}$$

Catalysts suitable for the present invention are those which employ a zeolite having a constraint index from 1.0 to 12.0. Constraint Index values for some typical zeolites within the scope of this invention are:

| catalyst | Constraint Index |
|---|---|
| ZSM-5 | 8.3 |
| ZSM-11 | 8.7 |
| ZSM-35 | 4.5 |
| ZSM-12 | 2 |
| ZSM-38 | 2 |

The said catalysts are described, for example, in U.S. Pat. No. 3,702,886 (ZSM-5), U.S. Pat. No. 3,709,979 (ZSM-11), U.S. Pat. No. 3,832,449 (ZSM-12), U.S. application Ser. No. 358,192 filed May 7, 1973 (ZSM-21), U.S. application Ser. No. 528,061 filed Nov. 29, 1974 (ZSM-35), U.S. application Ser. No. 528,060 filed Nov. 29, 1974 (ZSM-38), the entire contents of which are incorporated herein by reference. It is particularly advantageous to use ZSM-5-catalysts, of the type described in U.S. Pat. No. 3,702,886.

The methyl phenols can be isomered both in the gaseous phase and in the liquid phase. The catalysts are slowly deactivated by carbon deposition in the course of the reaction. This is delayed when working in the liquid phase so that this type of operation will generally be preferred. It also allows substantially higher throughput rates than a process carried out in the gaseous phase. The process is preferably carried out under elevated pressures of about 45 to 80 bar, in particular 50 to 60 bar. If necessary, the catalyst is regenerated by burning the deposited carbon with air at controlled temperatures, for example 500° C. It then exhibits its complete activity again.

The isomerisation treatments are carried out at temperatures of 350° to 450° C., advantageously 380° to 420° C., it being possible to compensate the abatement of the catalyst activity by increasing the reaction temperature in the course of the reaction. Temperatures above about 450° C. are not beneficial since the selectivity of the reaction decreases there and the catalysts are deactivated relatively quickly, particularly when working in the gaseous phase. A selectivity of more than 95% can generally be achieved. The hourly flow rate can amount to up to about 5 l/l catalyst volume, advantageously about 2.5 to 2.8 l/l when working in the liquid phase.

Whereas disproportionation to phenol, obtionally cresol and higher alkylated products is invariably found to a considerable extent in the processes described hitherto for the isomerisation of alkyl phenols with the aid of aluminium oxide or aluminium silicate catalysts, virtually no disproportionation, but instead only the desired isomerisation, surprisingly takes place in the process according to the invention.

EXAMPLE 1

100 g of o-cresol were introduced together with 50 g of pulverulent catalyst ZSM-11 into an autoclave provided with a stirring mechanism. The mixture was heated to 360° C. and was maintained at this temperature for one hour.

The reaction mixture obtained after cooling had the following composition:

| | |
|---|---|
| phenol | 4.4% by weight |
| o-cresol | 33.3% by weight |
| m-cresol | 42.3% by weight |
| p-cresol | 15.6% by weight |
| 2,5-xylenol | 1.5% by weight |
| 2,4-xylenol | 1.2% by weight |
| 2,6-xylenol | 0.4% by weight |
| 3,4-xylenol | 0.9% by weight |
| trimethylphenols | 0.4% by weight |

EXAMPLE 2

150 ml of the zeolite ZSM-5 processed to 4 mm pellets were introduced into an electrically heatable tube reactor. Once the reaction zone had been heated to 440° C. in a nitrogen stream, o-cresol was passed over the catalyst at a volumetric flow rate of 0.2 1/1 catalyst·h. The reaction mixture obtained after cooling had the following composition:

| | |
|---|---|
| phenol | 1.5% by weight |
| o-cresol | 47.5% by weight |
| m-cresol | 35.1% by weight |
| p-cresol | 14.4% by weight |
| 2,5-xylenol | 0.7% by weight |
| 2,4-xylenol | 0.4% by weight |
| 2,6-xylenol | 0.2% by weight |
| 2,3-xylenol | 0.1% by weight |
| 3,4-xylenol | 0.1% by weight |

Space-time yield m/p-cresol: 0.1 kg/l·h.

EXAMPLE 3

50 ml of a ZSM-5-catalyst were introduced in the form of 4 mm pellets into a vertically arranged, electrically heatable pressure-resistant tube reactor. In order to ensure that the reactor was uniformly filled with liquid, the starting material was pumped through the reactor from the bottom to the top. Somme o-cresol was reacted with a volumetric flow rate of 2.8 1/1 catalyst·h at a temperature of 380° C. and under a pressure of 60 bar.

The reaction product obtained had the following composition:

| | |
|---|---|
| phenol | 1.3% by weight |
| o-cresol | 59.0% by weight |
| m-cresol | 28.3% by weight |
| p-cresol | 10.1% by weight |
| 2,5-xylenol | 0.3% by weight |
| 2,4-xylenol | 0.2% by weight |
| 2,6-xylenol | 0.4% by weight |
| 3,4-xylenol | 0.4% by weight |

Space-time yield m/p-cresol: 1.08 kg/l·h.

EXAMPLE 4

Some o-cresol was reacted in the apparatus described in Example 3 with a volumetric flow rate of 2.5 1/1 catalyst·h at 420° C. and 60 bar over a zeolite of the ZSM-12 type. The reaction mixture obtained consisted of:

| | |
|---|---|
| phenol | 3.9% by weight |
| o-cresol | 53.4% by weight |
| m-cresol | 27.7% by weight |
| p-cresol | 11.1% by weight |
| 2,5-xylenol | 1.1% by weight |
| 2,4-xylenol | 1.1% by weight |
| 2,6-xylenol | 0.6% by weight |
| 2,3-xylenol | 0.5% by weight |
| 3,4 xylenol | 0.4% by weight |
| trimethylphenols | 0.2% by weight |

Space-time yield m/p-cresol: 0.97 kg/l·h.

EXAMPLE 5

In comparison, o-cresol was reacted as described in Example 3, but in the presence of a zeolite X and a zeolite A, respectively. In both cases the disproportionation of the o-cresol to phenol and higher alkylated phenols precedes preferred compared to isomerisation.

What we claim is:

1. In a process for isomerisation of o-cresol to m-cresol in the presence of an alumina and silica containing catalyst at elevated temperatures, the improvement which comprises reacting the o-cresol at temperatures of about 350° to 450° C. in the presence of an acidly acting crystalline aluminosilicate zeolite of the ZSM-type with a composition of oxides and water in the molar ratio of $1\pm0.4$ $M_2O/n:Al_2O_3:5-100$ $SiO_2:0-60$ $H_2O$, M representing a cation having a valence of n.

2. The process of claim 1 wherein the zeolite has a composition of $0.9\pm0.2$ $M_2O/n:Al_2O_3:5-100$ $SiO_2:0-40$ $H_2O$.

3. The process of claim 1 wherein the o-cresol is reacted under a pressure of between about 45 to 80 bar.

4. The process of claim 2 wherein the o-cresol is reacted under a pressure of between about 50 to 60 bar.

* * * * *